United States Patent
Barcelo et al.

(10) Patent No.: US 9,592,001 B2
(45) Date of Patent: Mar. 14, 2017

(54) IMPLANTABLE NANOSENSOR

(75) Inventors: Steven Barcelo, Palo Alto, CA (US); Zhiyong Li, Foster City, CA (US); Ansoon Kim, Mountain View, CA (US); Gary Gibson, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 269 days.

(21) Appl. No.: 14/406,601

(22) PCT Filed: Jul. 29, 2012

(86) PCT No.: PCT/US2012/048754
§ 371 (c)(1),
(2), (4) Date: Dec. 9, 2014

(87) PCT Pub. No.: WO2014/021809
PCT Pub. Date: Feb. 6, 2014

(65) Prior Publication Data
US 2015/0173656 A1    Jun. 25, 2015

(51) Int. Cl.
*G01J 3/44* (2006.01)
*A61B 5/1459* (2006.01)
*G01N 21/65* (2006.01)
*A61B 5/00* (2006.01)

(52) U.S. Cl.
CPC .......... *A61B 5/1459* (2013.01); *A61B 5/0075* (2013.01); *A61B 5/6862* (2013.01); *G01N 21/658* (2013.01)

(58) Field of Classification Search
CPC ... G01J 3/02; G01J 3/44; G01N 21/65; G01N 21/658; G01N 2021/656; A61B 5/1459; A61B 5/00
See application file for complete search history.

(56) References Cited

U.S. PATENT DOCUMENTS

| 7,172,622 B2 | 2/2007 | Weber et al. |
| 7,302,289 B2 | 11/2007 | Crowley |
| 7,524,671 B2 | 4/2009 | Clarke et al. |
| 8,045,152 B2 | 10/2011 | Halas et al. |
| 8,197,756 B2 | 6/2012 | Pison et al. |

(Continued)

FOREIGN PATENT DOCUMENTS

| CN | 102333478 A | 1/2012 |
| WO | WO-2011029886 | 3/2011 |
| WO | WO-2011078794 | 6/2011 |

OTHER PUBLICATIONS

Supplementary European Search Report, Feb. 8, 2016, EP Patent Application No. 12882012.3, 7 pages.

(Continued)

*Primary Examiner* — Abdullahi Nur
(74) *Attorney, Agent, or Firm* — North Shore Associates

(57) ABSTRACT

An implantable nanosensor includes a stent to be implanted inside a fluid conduit. The stent has a well in a surface of the stent. The implantable nanosensor further includes a nanoscale-patterned sensing substrate disposed in the well. The nanoscale-patterned sensing substrate is to produce an optical scattering response signal indicative of a presence of an analyte in a fluid carried by the fluid conduit when interrogated by an optical stimulus signal.

15 Claims, 5 Drawing Sheets

(56) References Cited

U.S. PATENT DOCUMENTS

| | | |
|---|---|---|
| 2002/0161430 A1 | 10/2002 | Jang |
| 2004/0180379 A1 | 9/2004 | Van Duyne et al. |
| 2007/0115474 A1 | 5/2007 | Chaton et al. |
| 2008/0214913 A1 | 9/2008 | Van Gogh et al. |
| 2009/0118605 A1 | 5/2009 | Van Duyne et al. |
| 2011/0264190 A1 | 10/2011 | McClain et al. |
| 2012/0059232 A1 | 3/2012 | Gross et al. |
| 2012/0092660 A1 | 4/2012 | Wu et al. |
| 2012/0164745 A1 | 6/2012 | Fu et al. |
| 2012/0309080 A1* | 12/2012 | Cunningham ......... G02B 1/005 435/288.7 |

OTHER PUBLICATIONS

Anker J.N. et al., Biosensing with Plasmonic Nanosensors, (Research Paper), Nature Materials, Jun. 2008, pp. 442-453, vol. 7. http://chemgroups.northwestern.edu/vanduyne/pdf/Nature%20Materials%207_442-453_2008.pdf.

El-Ansary, A. et al., Nanoparticles as Biochemical Sensors, (Research Paper), Nanotechnology, Science and Applications, Dove Press Journal, Sep. 22, 2010, pp. 65-76. http://www.ceet.niu.edu/cecourse/UEET%20235/NSA-8199-nanoparticies-as-biochemical-sensors_092210.pdf.

Hongki Yoo et al., "Intra-arterial catheter for simultaneous microstructural and molecular imaging in vivo," Nature Medicine, vol. 17, No. 12, Dec. 2011, pp. 1680-1685.

Jonathan M Yuen et al., "Transcutaneous Glucose Sensing by Surface-Enhanced Spatially Offset Raman Spectroscopy in a Rat Model," Anal. Chem. 2010, vol. 82, pp. 8382-8385.

Ke Ma et al., "In Vivo, Transcutaneous Glucose Sensing Using Surface-Enhanced Spatially Offset Raman Spectroscopy: Multiple Rats, Improved Hypoglycemic Accuracy, Low Incident Power, and Continuous Monitoring for Greater than 17 Days," Anal. Chem., 2011, vol. 83, pp. 9146-9152.

* cited by examiner

US 9,592,001 B2

IMPLANTABLE NANOSENSOR

CROSS-REFERENCE TO RELATED APPLICATIONS

N/A

STATEMENT REGARDING FEDERALLY SPONSORED RESEARCH OR DEVELOPMENT

N/A

BACKGROUND

Detection and identification (or at least classification) of unknown substances have long been of great interest and have taken on even greater significance in recent years. Among methodologies that hold particular promise for precision detection and identification are various forms of spectroscopy. Spectroscopy may be used to analyze, characterize and identify a substance or material using one or both of an absorption spectrum and an emission spectrum that results when the material is illuminated by a form of electromagnetic radiation (e.g., visible light). The absorption and emission spectra produced by illuminating the material determine a spectral 'fingerprint' of the material. In general, the spectral fingerprint is characteristic of the particular material to facilitate identification of the material. Among the most powerful of optical emission spectroscopy techniques are those based on Raman-scattering.

Scattering spectroscopy is an important means of identifying, monitoring and characterizing a variety of analyte species (i.e., analytes) ranging from relatively simple inorganic chemical compounds to complex biological molecules. Among the various types of scattering spectroscopy are methodologies that exploit Raman scattering and scattering due to fluorescence (e.g., fluorescence scattering) from an analyte. In general, scattering spectroscopy employs a signal to excite the analyte that, in turn, produces a response or scattered signal that is dependent on a characteristic (e.g., constituent elements of) the analyte. By detecting and analyzing the scattered signal (e.g., using spectral analysis), the analyte may be identified and even quantified, in some instances.

BRIEF DESCRIPTION OF THE DRAWINGS

Various features of examples in accordance with the principles described herein may be more readily understood with reference to the following detailed description taken in conjunction with the accompanying drawings, where like reference numerals designate like structural elements, and in which.

Figure 1:
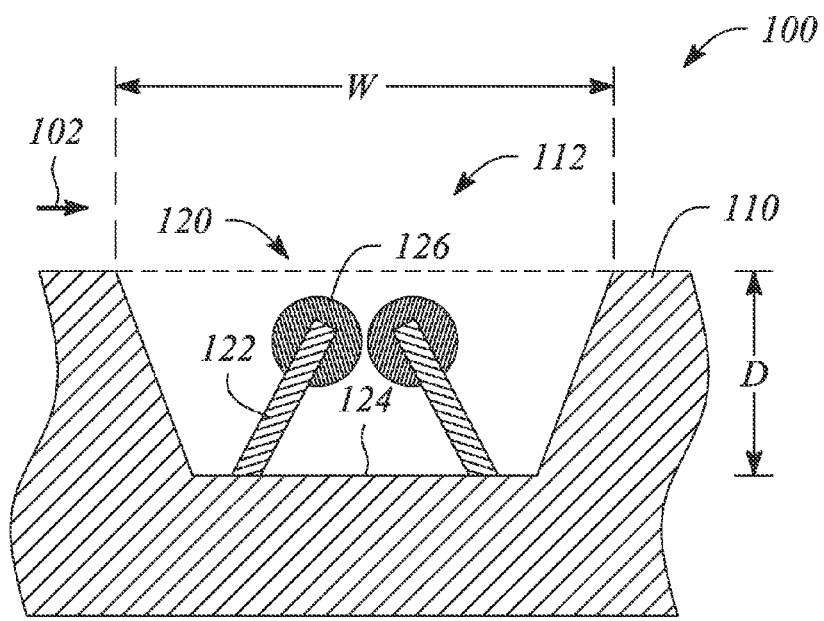
FIG. 1 illustrates a cross sectional view of a portion of an implantable nanosensor, according to an example consistent with the principles described herein.

Certain examples have other features that are one of in addition to and in lieu of the features illustrated in the above-referenced figures. These and other features are detailed below with reference to the above-referenced figures.

DETAILED DESCRIPTION

Examples in accordance with the principles described herein provide implantable detecting or sensing of various analytes. In particular, examples in accordance with the principles described herein provide sensing of analytes by an implantable nanosensor using scattering spectroscopy. In some examples, the implantable nanosensor may provide substantially continuous, in vivo monitoring of analytes (e.g., biological species). Moreover, the implantable nanosensor may provide intimate contact with a fluid (e.g., blood) containing or carrying the analyte without substantial interference with the fluid or with fluid flow.

Examples of the principles described herein employ scattering spectroscopy to detect or sense the presence of a target species or analyte. Herein, applicable forms of scattering spectroscopy include, but are not limited to, surface enhanced Raman spectroscopy (SERS), surface enhanced coherent anti-stokes Raman scattering (SECARS), various spatially offset and confocal versions of Raman spectroscopy, fluorescence spectroscopy (e.g., using fluorescent labels or tags), and direct monitoring of plasmonic resonances. The scattering spectroscopy may provide detection and in some examples, quantification of the analyte. In particular, the detection or sensing may be provided for an analyte that is either absorbed onto or closely associated with a surface of the implantable nanosensor, according to various examples. Herein, scattering spectroscopy will generally be described with reference to Raman-scattering optical spectroscopy for simplicity of discussion and not by way of specific limitation, unless otherwise indicated.

Raman-scattering optical spectroscopy or simply Raman spectroscopy employs an emission spectrum or spectral components thereof produced by inelastic scattering of photons by an internal structure of the material being illuminated. These spectral components contained in a response signal (e.g., a Raman scattering signal) produced by the inelastic scattering may facilitate determination of the material characteristics of an analyte species including, but not limited to, identification of the analyte. Surface enhanced Raman-scattering (SERS) optical spectroscopy is a form of Raman spectroscopy that employs a Raman-active surface. SERS may significantly enhance a signal level or intensity of the Raman scattering signal produced by a particular analyte species. In particular, in some instances, the Raman-active surface comprises regions associated with the tips of nanostructures such as, but not limited to, nanofingers or nanorods. The tips of the nanofingers or nanorods may serve as nanoantennas to one or both of concentrate an illumination field and amplify a Raman emission leading to further enhancement of the strength of the Raman scattering signal, for example.

In some examples of SERS, a SERS surface comprising a plurality of nanorods is configured to enhance production and emission of the Raman scattering signal from an analyte. Specifically, an electromagnetic field associated with and surrounding the nanorods (e.g., tips of the nanorods) in a 'Raman-active' configuration may enhance Raman scattering from the analyte, in some examples. A relative location of the nanorods themselves as well as tips of the nanorods in the Raman-active configuration may provide enhanced Raman scattering.

A 'nanorod' or equivalently 'nanofinger' herein is defined as an elongated, nanoscale structure having a length (or height) that exceeds by more than several times a nanoscale cross sectional dimension (e.g., width) taken in a plane perpendicular to the length (e.g., length>about 5 times the width). In general, the length of the nanorod is much greater than the nanorod width or cross sectional dimension. In some examples, the length exceeds the cross sectional dimension (or width) by more than a factor of 5 or 10. For example, the width may be about 40 nanometers (nm) and the height may be about 400 nm. In another example, the width at a base of the nanorod may range between about 20 nm and about 100 nm and the length may be more than about a 1 micrometer (µm). In another example, the nanorod may be conical with a base having a width ranging from between about 100 nm and about 500 nm and a length or height that may range between about one and several micrometers.

In various examples, nanorods of the plurality may be grown (i.e., produced by an additive process) or produced by etching or a subtractive process. For example, the nanorods may be grown as nanowires using a vapor-liquid-solid (VLS) growth process. In other examples, nanowire growth may employ one of a vapor-solid (V-S) growth process and a solution growth process. In yet other examples, growth may be realized through directed or stimulated self-organization techniques such as, but not limited to, focused ion beam (FIB) deposition and laser-induced self assembly. In another example, the nanorods may be produced by using an etching process such as, but not limited to, reactive ion etching, to remove surrounding material leaving behind the nanorods. In yet other examples, various forms of imprint lithography including, but not limited to, nanoimprint lithography as well as various techniques used in the fabrication of micro-electromechanical systems (MEMS) and nano-electromechanical systems (NEMS) are applicable to the fabrication of the nanorods and various other elements described herein.

A 'nanoparticle' herein is defined as a nanoscale structure having substantially similar dimensions of length, width and depth. For example, the shape of a nanoparticle may be a cylinder, a sphere, an ellipsoid, or a faceted sphere or ellipsoid, or a cube, an octahedron, a dodecahedron, or another polygon. The nanoparticle may comprise a substantially irregular three-dimensional shape, in other examples. The size of the nanoparticle may range from about 5 nm to about 200 nm, for example, in diameter or dimension. In some examples, the nanoparticle dimensions may be within a range of about 50 nm to about 100 nm, or about 25 nm to about 100 nm, or about 100 nm to about 200 nm, or about 10 nm to about 150 nm, or about 20 nm to about 200 nm. Further as defined herein, the 'nanoparticle' is distinguished from a 'nanoparticle catalyst' or 'catalyst nanoparticle' and a layer or coating of nanoparticles, according to some examples.

Herein, a 'well' is defined as a depression purpose-formed in a surface. Further by definition herein, the well has an opening at a first end of the well. The well has a lateral extent or 'width' defined as a dimension across an opening of the well at the surface into which the well is formed, for example. In some examples, the width of the well may be between about 10 nanometers (nm) to greater than about 1000 nm. For example, the well may have a width of about 300 nm. In another example, the well width is 400 nm. By 'purpose-formed' is it meant that the well is created for an intended purpose as opposed to a depression that may result from damage or as a natural part of a fabrication process that yields the surface.

In addition to the lateral extent or width, the well has a depth, by definition. The depth is greater, and in some examples, much greater, than a surface roughness of the surface into which the well is purpose-formed. In particular, the depth and the width of the well together distinguish the well herein from features of the surface (e.g., indentations) that may occur accidentally or naturally, for example. In some examples, the depth is less than about the width of the well. The depth may be between about 20 nm and about 300 nm, for example, while the width may be greater than 300 nm. In other examples, the depth is generally greater than the width of the opening of the well. For example, the depth may be greater than about 110% of the well opening width. In another example, the depth may be between about 105% and about 150% of the width. For example, the well may have a width of between about 500 nm and 550 nm and the well may have a depth that is greater than 550 nm.

In some examples, the depth of the well is greater than a length of a nanorod located within the well (e.g., a nanorod of a SERS surface disposed in the well). A depth that is greater than a length of the nanorod may provide protection of the nanorod and nanorod tip from mechanical damage, for example. In other examples, the depth of the well is greater than 10% but less than about 100% of a length of the nanorod. In other words, a portion of the nanorod extends above the surface into which the well is purpose-formed.

The well may be formed (i.e., purpose-formed) by any number of circuit fabrication techniques including, but not limited to, one or more of etching (wet or dry), nanoimprint lithography and selective deposition. For example, a silicon substrate may be masked and exposed to a potassium hydroxide (KOH) solution to etch an exposed surface of the silicon and form the well. Etching a silicon substrate with KOH may produce a well with sloped or tapered sides and a flat bottom, for example. Plasma etching and especially reactive ion etching (RIE) may be employed in a directed fashion to produce a variety of specific tapered well profiles. Nanoimprint lithography may be employed variously in either subtractive or additive methods to form the well in a surface. Deposition, such as epitaxial deposition, may be used to build up a surface surrounding the well, for example.

Further, as used herein, the article 'a' is intended to have its ordinary meaning in the patent arts, namely 'one or more'. For example, 'a nanosensor' means one or more nanosensors and as such, 'the nanosensor' means 'the nanosensor(s)' herein. Also, any reference herein to 'top', 'bottom', 'upper', 'lower', 'up', 'down', 'front', back', 'left' or 'right' is not intended to be a limitation herein. Herein, the term 'about' when applied to a value generally means within the tolerance range of the equipment used to produce the value, or in some examples, means plus or minus 10%, or plus or minus 5%, or plus or minus 1%, unless otherwise expressly specified. Moreover, examples herein are intended to be illustrative only and are presented for discussion purposes and not by way of limitation.

FIG. 1 illustrates a cross sectional view of a portion of an implantable nanosensor 100, according to an example consistent with the principles described herein. As illustrated, the implantable nanosensor 100 is configured to sense an analyte in a fluid flowing through or adjacent to the implantable nanosensor 100. An arrow 102 in FIG. 1 illustrates fluid flow past the implantable nanosensor 100, for example.

As illustrated, the implantable nanosensor 100 comprises a stent 110. In particular, FIG. 1 illustrates a portion of a wall of the stent 110. The stent 100 is configured to be implanted inside a fluid conduit (not illustrated), according to various examples. In some examples, the stent 110 comprises a hollow structure that is configured to allow the fluid flowing in the fluid conduit to pass through an interior portion (e.g., a hollow interior) of the stent 110. For example, the fluid may flow into a first end and along a path through the hollow interior that is substantially aligned with a central axis of the stent 110 and then exit at a second end of the stent 110. In other examples, the stent 110 may not be hollow, in which case the stent 110 is configured to allow for fluid flow around but not through the stent 110. In yet other examples, the stent 110 may comprise a hollow or a substantially hollow structure that is configured to provide for fluid flow both through the hollow interior and around an outside of the stent 110.

According to various examples, the stent 110 has a well 112 in a surface of the stent 110 (i.e., a stent wall). The well 112 is a depression in the stent wall, by definition herein. The well 112 may have a depth D that is less than a width W of an opening of the well in the surface of the stent 110, according to some examples. In other example, a depth D of the well may be greater than the opening width W. In some examples, the stent 110 may have a plurality of wells 112. In some examples, the well 112 may have an opening that substantially faces toward an interior or central axis of the stent 110. For example, when the stent 110 comprises a hollow structure, the well 112 may face the hollow interior of the stent 110. In other examples, the well 112 may face toward an outside of the stent 110.

In some examples, the stent 110 may comprise a tubular structure that is substantially hollow. A cross sectional shape of the tubular structure may be either substantially circular (e.g., circular, elliptical, semi-circular, etc.) or substantially non-circular (e.g., rectangular, square, generally polygonal or faceted, etc.), according to various examples. In some examples, the tubular structure may have a fixed or substantially fixed diameter. In other examples, the tubular structure may be configured to expand and substantially conform to an inside surface or wall of the fluid conduit. For example, the fluid conduit may comprise a blood vessel and the tubular structure of the stent 110 may be expandable to conform to an inside surface of the blood vessel.

In some examples, expansion of the tubular structure of the stent 110 may facilitate retaining or securing the stent 110 in place within the fluid conduit. For example, the expansion may press portions of the tubular structure of the stent 110 against a wall of the fluid conduit such that a friction between the stent 110 and the fluid conduit wall resists a force imparted on the stent 110 by the fluid flowing within the fluid conduit. Further, the expansion of the tubular structure of the stent 110 may facilitate fluid flow through an interior of the tubular structure. For example, the expanded substantially tubular structure may provide an opening through the tubular structure that is similar in diameter to that of the fluid conduit itself. As such, the stent 110 may not interfere in a substantial manner with fluid flow in the fluid conduit, according to some examples.

According to some examples, the expandable tubular structure of the stent 110 may comprise a mesh such as, but not limited to, a tubular wire mesh. For example, the wire mesh may be arranged in an interconnected diamond pattern. In other examples, another wire mesh pattern including, but not limited to, a serpentine pattern may be employed to realize the mesh. Wire of the tubular wire mesh may comprise a metal such as, but not limited to, stainless steel and a cobalt chromium alloy, for example. In other examples, a polymer or plastic string or wire-like material may be used.

According to other examples, the expandable tubular structure may comprise a folded tubular structure. For example, the folded tubular structure may comprise folds of substantially planar material. The folds may provide for the expansion, according to some examples. In yet other examples, the expandable tubular structure of the stent 110 may be realized by another means including, but not limited to, sections that slide past one another to provide expansion.

Figure 2A:
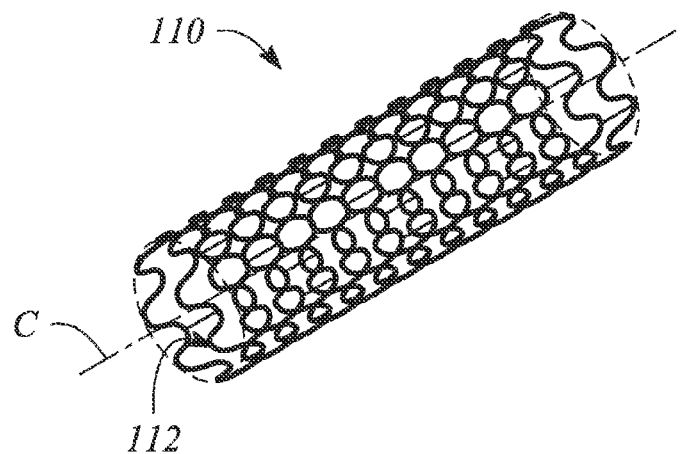
FIG. 2A illustrates a perspective view of a stent of the implantable nanosensor, according to an example consistent with the principles described herein.

FIG. 2A illustrates a perspective view of a stent 110 of the implantable nanosensor 100, according to an example consistent with the principles described herein. As illustrated, the stent 110 comprises a serpentine wire mesh. While illustrated as a serpentine wire mesh, a variety of different wire mesh configurations may be employed to realize the stent 110, according to various examples. A well, e.g., similar to well 112 illustrated in FIG. 1, may be formed into a surface of the wire of the wire mesh, for example. In some examples, a plurality of wells (not illustrated) may be located at various points or locations along wires of the wire of the wire mesh. The wells are oriented to open toward an interior of the stent 110. In particular, the wells are located on a surface of the wire of the wire mesh that points toward a central axis C of the stent 110, as illustrated.

Figure 2B:
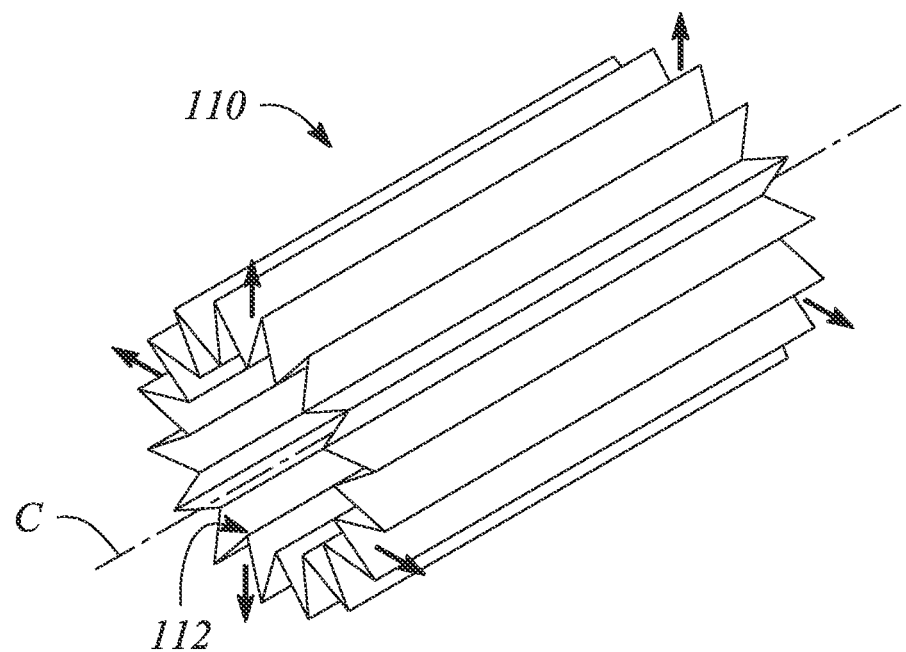
FIG. 2B illustrates a perspective view of a stent of the implantable nanosensor, according to another example consistent with the principles described herein.

FIG. 2B illustrates a perspective view of a stent 110 of the implantable nanosensor 100, according to another example consistent with the principles described herein. In particular, the stent 110 illustrated in FIG. 2B is an expandable tubular structure comprising a folded, substantially planar material. The folds may be provided by hinges or a hinge-like membrane that connect planar sections of the material, for example. The folds are configured to unfold when the stent 110 is implanted enabling the stent 110 to expand. The unfolding may enable the stent 110 to substantially conform to an inside wall of the fluid conduit, for example. Unfolding is illustrated by heavy arrows pointing away from a central axis C of the stent 110. A well, e.g., similar to well 112 illustrated in FIG. 1, may be formed into a surface of the substantially planar material, for example.

Figure 2C:
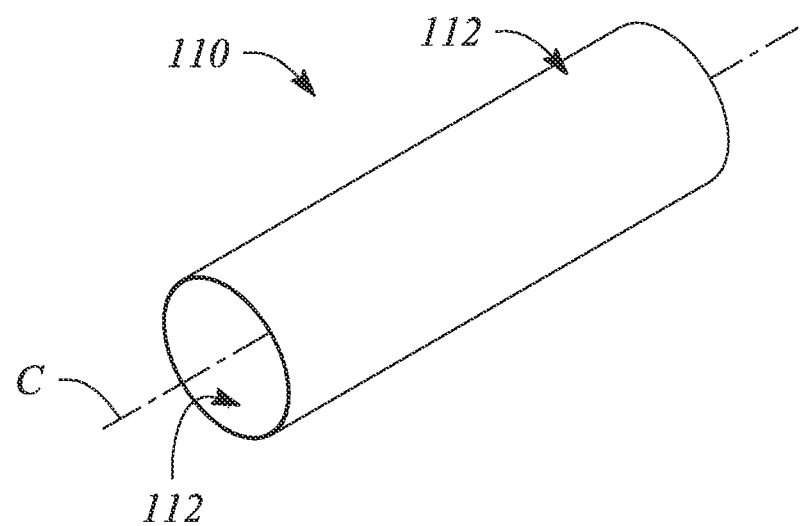
FIG. 2C illustrates a perspective view of a stent of the implantable nanosensor 100, according to yet another example consistent with the principles described herein.

FIG. 2C illustrates a perspective view of a stent 110 of the implantable nanosensor 100, according to yet another example consistent with the principles described herein. As illustrated in FIG. 2C, the stent 110 comprises a substantially non-expandable tubular structure. The substantially non-expandable tubular structure may comprise a tube of either a rigid or a semi-rigid material, in some examples. For example, the tube may comprise a metal tube (e.g., stainless steel, nitinol alloy, etc.) or a polymer tube. The tube may have an outside diameter that is smaller, and in some examples much smaller, than an inside diameter of the fluid conduit, according to some examples. FIG. 2C illustrates wells 112 located on both an outside surface and an inside surface of the stent 110.

Referring again to FIG. 1, the implantable nanosensor 100 further comprises a nanoscale patterned sensing substrate 120. According to various examples, the nanoscale patterned sensing substrate 120 is disposed in the well 112 in the surface the stent 110. The nanoscale-patterned sensing substrate 120 is configured to produce an optical scattering response signal indicative of the presence of an analyte in a fluid carried by the fluid conduit. In particular, the optical scattering response signal may be produced when the nanoscale-patterned sensing substrate 120 is interrogated by an optical stimulus signal, according to various examples.

In some examples, the fluid carried by the fluid conduit is flowing past the well 112 and the nanoscale-patterned sensing substrate 120 therein. For example, when the fluid conduit comprises a blood vessel, the fluid flowing past the well 112 may comprise blood and the implantable nanosensor 100 may provide in vivo sensing of an analyte carried in the blood. In other examples, the fluid conduit carrying blood may be a tube connected to a blood vessel (e.g., external to an organism), in which case the analyte sensing may not be in vivo.

In some examples, the nanoscale-patterned sensing substrate 120 comprises a surface enhanced Raman spectroscopy (SERS) substrate. In these examples, the optical scattering response signal may comprise a SERS scattering signal. In other examples, the nanoscale-patterned sensing substrate 120 may comprise another optical scattering signal including, but not limited to, those signals associated with one or both of infrared spectroscopy and fluorescence spectroscopy. For example, the nanoscale-patterned sensing substrate 120 may comprise tagged structures configured to produce a fluorescence signal when the analyte is present.

In some examples, the SERS sensing substrate may comprise a plurality of nanorods 122 arranged in an array. The nanorods 122 each have a free end that is opposite to an end that is attached to a support 124, according to some examples. In some examples, the support 124 may be a bottom surface of the well 112. In other examples, the support 124 may comprise a substrate (e.g., a carrier substrate) that provides support for the nanorods 122. For example, the substrate may be bonded to a bottom surface of the well 112. In some examples, the nanorods 122 are rigidly attached to the support 124 at the fixed end. In other examples, the nanorods 122 are indirectly attached to the support 124 through an intermediate material or layer, for example.

In some examples, a nanorod 122 in the array has a metallic tip at the free end. The metallic tip may be configured to absorb the analyte, for example. In some examples, the metallic tip at the free end of the nanorod 122 may be functionalized. In particular, the nanorod 122 may be functionalized to preferentially bind to or provide selective absorption of a particular analyte species, for example.

In some examples, a nanorod 122 in the array may comprise a nanoparticle 126 attached to the free end in a vicinity of the tip. In some examples, a material of the nanoparticle 126 may differ from a material of the nanorod 122. For example, the tip may include a rounded metal (e.g., gold) nanoparticle 126 that remains from nanorod growth, for example. In some of these examples, the nanoparticle 126 may be configured to one or both of enhance Raman scattering and facilitate selective analyte adsorption (e.g., by functionalization). In particular, in some examples, the nanoparticle 126 comprises a material suitable for Raman enhancement. For example, the nanoparticle 126 may comprise a material such as, but not limited to, gold, silver, platinum, aluminum and copper.

In some examples, a nanorod 122 in the array comprises a plurality of the nanorod 122. As such, the plurality of the nanorod 122 may be arranged in a bundle, for example. As used herein, a 'bundle' is defined as a relatively small grouping or a small array. For example, the bundle may comprise two, three, four, five, six or more nanorods 122. The nanorods 122 of the bundle may be arranged such that the free ends and the fixed ends of the nanorods 122, respectively, are located at vertices of a polygon or a polyhedron (e.g., a digon, a trigon, a tetragon, a pentagon, a hexagon, and so on), according to various examples. In another example, a bundle may have up to about ten nanorods 122. In yet another example, the bundle may have less than about fifteen nanorods 122. Moreover, there may be a plurality of such bundles, in some examples.

Figure 3:
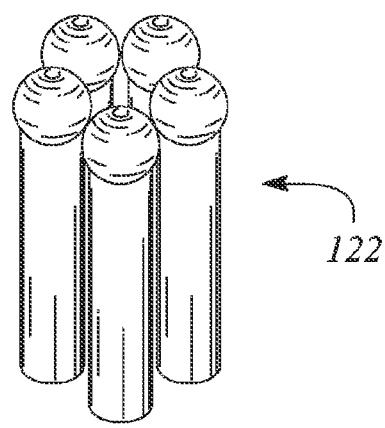
FIG. 3 illustrates a perspective view of a bundle of a plurality of nanorods, according to an example consistent with the principles described herein.

FIG. 3 illustrates a perspective view of a bundle of a plurality of nanorods 122, according to an example consistent with the principles described herein. The bundle illustrated in FIG. 3 comprises five nanorods 122. Further as illustrated, the plurality of nanorods 122 of the bundle is arranged as a pentagon. In other examples, the plurality of nanorods 122 may be arranged in a larger array (not illustrated). A larger array may have several tens of nanorods, hundreds of nanorods or even more, for example. The array, including both small arrays (e.g., bundles) and large arrays, may include, but is not limited to, a linear array or one-dimensional (1-D) array or a two-dimensional (2-D) array (e.g., a rectilinear array, a circular array, etc.).

The nanorods 122 in either the bundle or the array may be either touching one another or spaced apart from one another. For example, tips of the nanorods 122 in the bundle may be substantially touching or in close proximity, separated by a gap of a about a few nanometers or less. Further, nanorods 122 in either the bundle or the array may be tilted toward one another (e.g., see FIG. 1). The tilting may facilitate contact between the tips of the nanorods 122, for example. A spacing between nanorods 122 of the plurality when spaced apart within the bundle or the array may be either regular (i.e., a periodic spacing) or irregular (e.g., a substantially random spacing). For example, the nanorods 122 of the plurality may be arranged in a pair of substantially parallel, regular-spaced, linear arrays.

In some examples, the nanorod 122 may comprise a semiconductor. For example, the semiconductor may comprise doped or undoped (i.e., substantially intrinsic) silicon (Si) or germanium (Ge) or an alloy of Si and Ge. In other examples, the semiconductor may comprise gallium arsenide (GaAs), indium gallium arsenide (InGaAs), and gallium nitride (GaN), or various other III-V, II-VI, and IV-VI compound semiconductors. In other examples, the nanorod 122 may comprise a plastic or a polymer such as, but not limited to, polyurethane, poly(tert-butyl methacrylate) (P(tBMA)), polymethylmethacrylate (PMMA), polystyrene, polycarbonate or related plastics. In yet other examples, the nanorod 122 may comprise a metal such as, but not limited to, gold, silver, platinum, other noble metals, aluminum copper, or an alloy or a combination of two or more metals.

In accordance with some examples herein, the implantable nanosensor 100 further comprises a protective membrane. In some examples, the protective membrane is configured to cover or substantially cover an opening of the well 112. In some examples, the nanoscale-patterned sensing substrate 120 is attached to a surface of the well 112 (e.g., the bottom of the well) and the protective membrane covers the well opening above the attached nanoscale-patterned sensing substrate 120. In other examples, the nanoscale-patterned sensing substrate 120 disposed in the well 112 is attached to and supported by the protective membrane. In some examples, the protective membrane is a semipermeable membrane. In particular, the semipermeable protective membrane may be configured to facilitate passage of the analyte from the fluid conduit into the well 112.

In some examples, the semipermeable protective membrane comprises a biocompatible material. For example, the semipermeable protective membrane may comprise a polyurethane film. Other biocompatible materials that may be used in the semipermeable protective membrane include, but are not limited to, polyethylene glycol films, parylene-C (e.g., in an ultra thin layer), films comprising Nafion™, multilayer humic acids/ferric cation (HAs/$Fe^{3+}$) membranes, cation exchange membranes (CEM), charge mosaic membranes (CMM), bipolar membranes (BPM), anion exchange membranes (AEM), alkali anion exchange membranes (AAEM), and proton exchange membranes (PEM). Nafion™ is a sulfonated tetrafluoroethylene based fluoropolymer-copolymer product of Du Pont De Nemours and Company Corporation, Delaware. In some examples, the semipermeable protective membrane may be selective for a particular analyte, a class of analytes, or size range of analytes, for example.

Figure 4A:
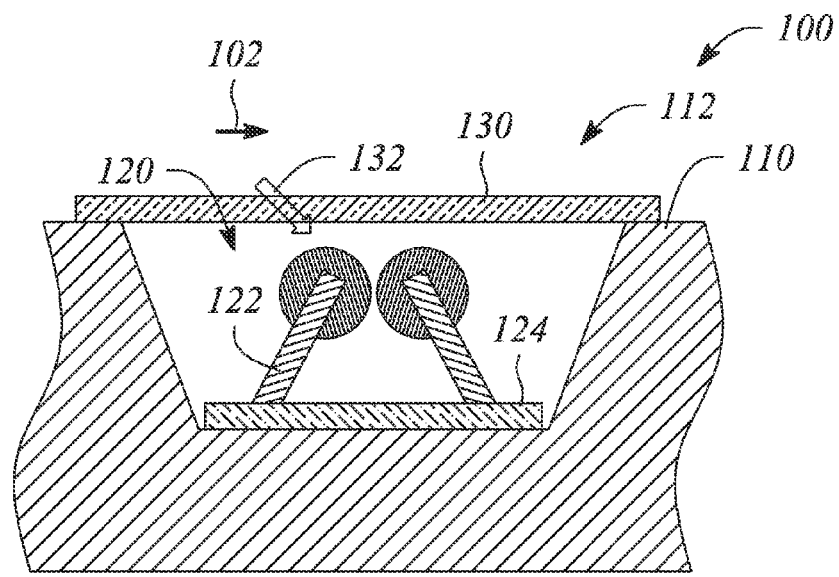
FIG. 4A illustrates a cross sectional view of a portion of an implantable nanosensor, according to an example consistent with the principles described herein.

FIG. 4A illustrates a cross sectional view of a portion of an implantable nanosensor 100, according to another example consistent with the principles described herein. In particular, FIG. 4A illustrates the implantable nanosensor 100 comprising the stent 110 (i.e., only a portion is illustrated), the nanoscale-patterned sensor substrate 120 and further the semipermeable protective membrane 130. As illustrated, the nanoscale-patterned sensor substrate 120 is attached to a bottom surface of a well 112 in the stent 110. The nanoscale-patterned sensor substrate 120 comprises nanorods 122 attached to a support substrate 124, as illustrated. Further as illustrated, is the semipermeable protective membrane 130 is depicted covering the well opening. A hollow arrow 132 illustrates movement of an analyte species from the flowing fluid 102 into the well 112.

Figure 4B:
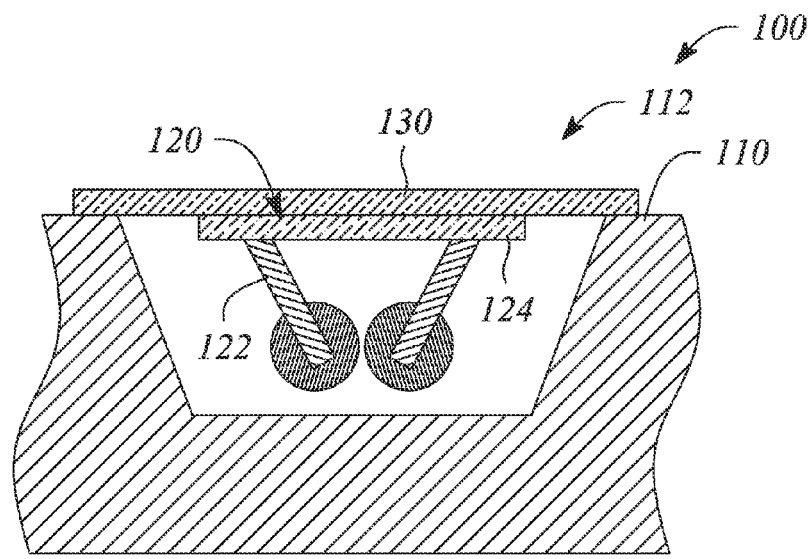
FIG. 4B illustrates a cross-sectional view of a portion of an implantable nanosensor, according to another example consistent with the principles described herein.

FIG. 4B illustrates a cross-sectional view of a portion of an implantable nanosensor 100, according to another example consistent with the principles described herein. As illustrated in FIG. 4A, the implantable nanosensor 100 comprises the stent 110 (i.e., only a portion is illustrated), the nanoscale-patterned substrate 120 disposed in the well 112 and the semipermeable protective membrane 130 covering the opening of the well 112 in the stent 110. Further as illustrated, the nanoscale-patterned sensor substrate 120 is attached to and supported by the semipermeable protective membrane 130. As illustrated, the nanoscale-patterned sensor substrate 120 comprises nanorods 122 attached to and supported by the support substrate 124. The support substrate 124 is attached to the semipermeable protective membrane 130. In some examples (not illustrated), the semipermeable protective membrane 130 itself may serve as the support substrate obviating a need for a separate support substrate 124, for example.

In some examples, the semipermeable protective membrane 130 illustrated in FIGS. 4A-4B is configured to protect the nanoscale-patterned sensing substrate 120 from damage by the fluid flowing in the fluid conduit. For example, the semipermeable protective membrane 130 may protect the nanoscale-patterned sensing substrate 120 from damage due to shear associated with the flowing fluid. The semipermeable protective membrane 130 may further protect the nanoscale-patterned sensing substrate 120 from the fluid itself or objects carried by the fluid. For example, the semipermeable protective membrane 130 may prevent portions of the fluid that may be corrosive to or that may otherwise be damaging to the nanoscale-patterned sensing substrate 120 from entering the well 112. The semipermeable protective membrane 130 may also screen objects (e.g., blood cells, plaque, large molecules, etc.) from entering the well 112 that may damage or interfere with operation of the nanoscale-patterned sensing substrate 120, in some examples.

Figure 5:
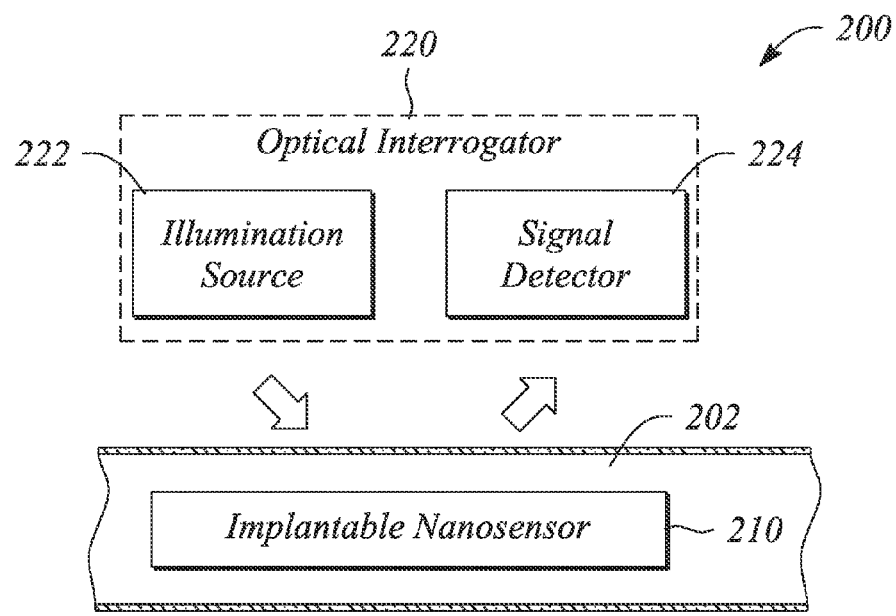
FIG. 5 illustrates a block diagram of a nanosensor system, according to an example consistent with the principles described herein.

FIG. 5 illustrates a block diagram of a nanosensor system 200, according to an example consistent with the principles described herein. As illustrated, the nanosensor system 200 comprises an implantable nanosensor 210. According to various examples, the implantable nanosensor 210 comprises a stent having a well and a nanoscale-patterned sensing substrate disposed in the well. The nanoscale-patterned sensing substrate is configured to produce an optical scattering response signal indicative of the presence of an analyte when interrogated by an optical stimulus signal. In some examples, the stent of the implantable nanosensor 210 is configured to be implantable inside a fluid conduit 202.

In some examples, the implantable nanosensor 210 is substantially similar to the implantable nanosensor 100 described above. In particular, the stent may be substantially similar to the stent 110 described above with respect to the implantable nanosensor 100. In some examples, the stent may comprise an expandable tubular structure such as, but not limited to, a tubular wire mesh. The well may be formed or otherwise provided in a surface of the wire of the wire mesh, for example.

Further, the nanoscale-patterned sensing substrate may be substantially similar to the nanoscale-patterned sensing substrate 120 described above with respect the implantable nanosensor 100, according to some examples. In particular, in some examples, the nanoscale-patterned sensing substrate comprises a surface enhanced Raman spectroscopy (SERS) substrate. The optical scattering response signal may be a Raman scattering signal produced by an interaction between the analyte and the SERS substrate, according to some examples.

In some examples, the implantable nanosensor 210 further comprises a protective membrane. The protective membrane is configured to cover an opening in the well, according to various examples. In some examples, the protective membrane is semipermeable to facilitate passage of the analyte from the fluid conduit into the well. In some examples, the protective membrane is substantially similar to the protective membrane 130 described above with respect to the implantable nanosensor 100.

In some examples, the implantable nanosensor 210 is configured to detect a plurality of different analytes. In some examples, the implantable nanosensor 210 is configured to distinguish between the different analytes. For example, the stent of the implantable nanosensor 210 may have a plurality of wells in the stent surface. A different nanoscale-patterned sensing substrate of a plurality of nanoscale-patterned substrates may be disposed in each of the wells of the plurality of wells. Further, one or more of the nanoscale patterned sensing substrates is functionalized to be selective for a different analyte of a plurality of analytes and to produce an optical scattering response signal indicative of the respective different analyte. Spatial separation between the wells may facilitate distinguishing an optical scattering response signal produced by a first analyte specific to a first nanoscale-patterned sensing substrate from an optical scattering response signal produced by a second analyte specific to a second nanoscale-patterned sensing substrate, for example.

As illustrated in FIG. 5, the nanosensor system 200 further comprises an optical interrogator 220. According to some examples, the optical interrogator 220 comprises an illumination source 222. The illumination source 222 is configured to illuminate the nanoscale-patterned sensing substrate of the implantable nanosensor 210. In particular, the illumination source 222 is configured to illuminate the nanoscale-patterned sensing substrate in vivo while the implantable nanosensor 210 is implanted in the fluid conduit. In some examples, the illumination source 222 is configured to produce an infrared optical signal to illuminate the nanoscale-patterned sensing substrate. For example, infrared radiation may penetrate biological tissue (e.g., human tissue) to a depth of about 10-15 millimeters (mm) facilitating in vivo illumination and interrogation of the implantable nanosensor 210. In other examples, the illumination source 222 is configured to produce an optical signal comprising other optical frequencies instead of or including infrared.

In some examples, the optical interrogator 220 further comprises signal detector 224. The signal detector 224 is configured detect the optical scattering response signal emitted by the implantable nanosensor 210 that is indicative of the analyte. For example, the signal detector 224 may be a Raman scattered signal detector configured to detect the Raman scattered signal emitted by the nanoscale-patterned sensing substrate configured as a SERS substrate. In some examples, one or both of the illumination source 222 and the signal detector 224 are external to the fluid conduit. For example, the fluid conduit may be a blood vessel and the illumination source 222 may be external to blood vessel (e.g., outside of the body containing the blood vessel). Similarly, the signal detector 224 may be external to the blood vessel, according to some examples. In other examples, one or both of the illumination source 222 and the signal detector 224 may be internal to the fluid conduit. For example, one or both of the illumination source 222 and the signal detector 224 may be an implantable along with the implantable nanosensor 210 inside the fluid conduit (e.g., blood vessel).

Figure 6:
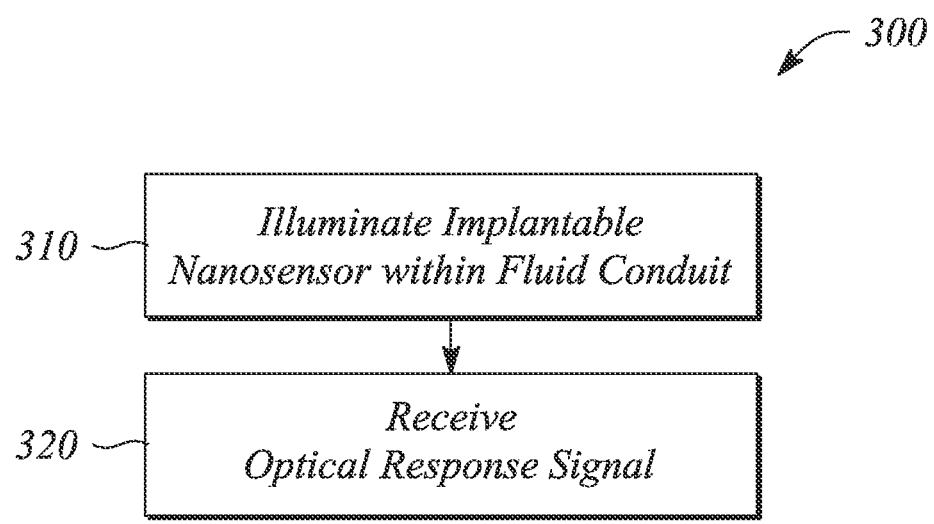
FIG. 6 illustrates a flow chart of a method of in vivo sensing using an implantable nanosensor, according to an example consistent with the principles described herein.

FIG. 6 illustrates a flow chart of a method 300 of in vivo sensing using an implantable nanosensor, according to an example consistent with the principles described herein. As illustrated, the method 300 of in vivo sensing comprises illuminating 310 an implantable nanosensor within a fluid conduit using an illumination source. In some examples, the implantable nanosensor is substantially similar to the implantable nanosensor 100, described above. In particular the implantable nanosensor comprises a stent having a well and a nanoscale-patterned sensing substrate disposed in the well. The nanoscale-patterned sensing substrate is configured to produce an optical scattering response signal indicative of the presence of an analyte when illuminated, according to various examples. In some examples, the illumination source is substantially similar to the illumination source 222 described above with respect to the nanosensor system 200, described above.

In some examples, the nanoscale-patterned sensing substrate comprises a surface enhanced Raman spectroscopy (SERS) substrate and the optical scattering response signal is a Raman scattered signal produced by an interaction between the analyte and the SERS substrate. For example, the SERS substrate may be substantially similar to the SERS substrate described above comprising nanorods 122 arranged in an array.

As illustrated in FIG. 6, the method 300 of in vivo sensing using an implantable nanosensor further comprising receiving 320 the optical response signal emitted by the nanoscale-patterned sensing substrate. In some examples, receiving 320 may be performed by a signal detector. For example, the signal detector may be substantially similar to the signal detector 224 described above with respect to the nanosensor system 200. In some examples, one or both of the illumination source and the signal detector are located external to the fluid conduit containing the implantable nanosensor.

Thus, there have been described examples of an implantable nanosensor, a nanosensor system and a method of in vivo sensing using an implantable nanosensor configured to sense an analyte in a fluid flowing in a fluid conduit. It should be understood that the above-described examples are merely illustrative of some of the many specific examples that represent the principles described herein. Clearly, those skilled in the art can readily devise numerous other arrangements without departing from the scope as defined by the following claims.

What is claimed is:
1. An implantable nanosensor comprising:
   a stent to be implanted inside a fluid conduit, the stent having a well in a surface of the stent; and
   a nanoscale-patterned sensing substrate disposed in the well, the nanoscale-pattered sensing substrate to produce an optical scattering response signal indicative of a presence of an analyte in a fluid carried by the fluid conduit when interrogated by an optical stimulus signal.

2. The implantable nanosensor of claim 1, wherein the nanoscale-patterned sensing substrate comprises a surface enhanced Raman spectroscopy (SERS) substrate, and wherein the optical scattering response signal is a Raman scattered signal.

3. The implantable nanosensor of claim 2, wherein the SERS substrate comprises a plurality of nanorods arranged in an array, a nanorod of the plurality having a metallic tip to absorb the analyte, the tip being at a free end of the nanorod opposite to an end that is attached to a support.

4. The implantable nanosensor of claim 1, wherein the fluid-carrying conduit comprises a blood vessel, the fluid being blood that comprises the analyte, the implantable nanosensor to provide in vivo sensing of the analyte.

5. The implantable nanosensor of claim 1, further comprising a protective membrane to cover an opening of the well, the protective membrane being semipermeable to facilitate passage of the analyte from the fluid conduit into the well.

6. The implantable nanosensor of claim 5, wherein the nanoscale-patterned sensing substrate disposed in the well is attached to and supported by the protective membrane.

7. The implantable nanosensor of claim 1, wherein the stent has a plurality of wells in the stent surface, a different nanoscale-patterned sensing substrate being disposed in some of the wells.

8. The implantable nanosensor of claim 7, wherein the different nanoscale-patterned sensing substrates are functionalized to be selective for different analytes of a plurality of analytes and to produce an optical scattering response signal indicative of the respective different analyte.

9. A nanosensor system comprising the implantable nanosensor of claim 1, the nanosensor system further comprising:

an illumination source to illuminate the nanoscale-patterned sensing substrate, illumination from the illumination source to produce the optical scattering response signal; and a signal detector to detect the optical scattering response signal emitted by the implantable nanosensor indicative of the analyte, wherein one or both of the illumination source and the signal detector are external to the fluid conduit.

10. A nanosensor system comprising:

an implantable nanosensor comprising a stent having a well and a nanoscale-patterned sensing substrate disposed in the well, the nanoscale-patterned sensing substrate to produce an optical scattering response signal indicative of a presence of an analyte; and an optical interrogator comprising an illumination source and a signal detector, the illumination source to illuminate the nanoscale-patterned sensing substrate with an optical stimulus signal, the signal detector to detect the optical scattering response signal, wherein the implantable nanosensor is to be implanted inside a fluid conduit, one or both of the illumination source and the signal detector being external to the fluid conduit.

11. The nanosensor system of claim 10, wherein the nanoscale-patterned sensing substrate comprises a surface enhanced Raman spectroscopy (SERS) substrate, and wherein the optical scattering response signal is a Raman scattered signal produced by an interaction between the analyte and the SERS substrate.

12. The nanosensor system of claim 10, wherein the implantable nanosensor further comprises a protective membrane to cover an opening of the well, the protective membrane being semipermeable to facilitate passage of the analyte from the fluid conduit into the well.

13. The nanosensor system of claim 10, wherein the stent has a plurality of separate wells in the surface, a different nanoscale-patterned sensing substrate of a plurality of the nanoscale-patterned sensing substrates being disposed in some of the separate wells, and wherein the different nanoscale-patterned sensing substrates are functionalized to be selective for a different analyte of a plurality of analytes and to produce an optical scattering response signal indicative of the respective different analyte.

14. A method of in vivo sensing using an implantable nanosensor, the method comprising:

illuminating the implantable nanosensor within a fluid conduit using an illumination source, the implantable nanosensor comprising a stent having a well and a nanoscale-patterned sensing substrate disposed in the well, the illuminated nanoscale-patterned sensing substrate producing an optical scattering response signal indicative of the presence of an analyte; and receiving the optical scattering response signal using a signal detector, wherein one or both of the illumination source and the signal detector are located external to the fluid conduit containing the implantable nanosensor.

15. The method of in vivo sensing using an implantable nanosensor of claim 14, wherein the nanoscale-patterned sensing substrate comprises a surface enhanced Raman spectroscopy (SERS) sensing substrate and wherein the optical scattering response signal is a Raman scattered signal produce by an interaction between the analyte and the SERS substrate.

\* \* \* \* \*